United States Patent
Hochgraeber

(10) Patent No.: US 10,031,112 B2
(45) Date of Patent: Jul. 24, 2018

(54) METHODS FOR INJECTING SAMPLES IN LIQUID CHROMATOGRAPHY, PARTICULARLY IN HIGH PERFORMANCE LIQUID CHROMATOGRAPHY

(71) Applicant: DIONEX SOFTRON GMBH, Germering (DE)

(72) Inventor: Hermann Hochgraeber, Offenberg-Neuhausen (DE)

(73) Assignee: DIONEX SOFTRON GMBH, Germering (DE)

( * ) Notice: Subject to any disclaimer, the term of this patent is extended or adjusted under 35 U.S.C. 154(b) by 0 days.

(21) Appl. No.: 15/596,738

(22) Filed: May 16, 2017

(65) Prior Publication Data

US 2017/0248557 A1    Aug. 31, 2017

Related U.S. Application Data

(60) Continuation of application No. 14/454,563, filed on Aug. 7, 2014, which is a division of application No.
(Continued)

(30) Foreign Application Priority Data

Jan. 25, 2008 (DE) .................. 10 2008 006 266

(51) Int. Cl.
   *G01N 30/20*    (2006.01)
   *G01N 30/32*    (2006.01)
   *G01N 30/02*    (2006.01)

(52) U.S. Cl.
   CPC ............. *G01N 30/20* (2013.01); *G01N 30/32* (2013.01); *G01N 2030/027* (2013.01); *G01N 2030/201* (2013.01)

(58) Field of Classification Search
   CPC .. G01N 30/20; G01N 30/32; G01N 2030/201; G01N 2030/027
   See application file for complete search history.

(56) References Cited

U.S. PATENT DOCUMENTS 3,530,721 A    9/1970   Hrdina
4,300,393 A   11/1981   Stearns
(Continued)

FOREIGN PATENT DOCUMENTS

| WO | WO2006083776 A2 | 8/2006 |
| WO | 2007109529 A2 | 9/2007 |
| WO | 2008005845 A2 | 1/2008 |

OTHER PUBLICATIONS

Fujinari, "New Alternative to Normal Phase Hplc Automation Using Methylene Chloride Mobile Phases: A Synchronized Dual Switching Valve Loop Injection System," Journal of High Resolution Chromatography & Chromatography Communications, Aug. 1988, pp. 595-598, No. 8, Heidelberg, W. Germany (4 pages).

Primary Examiner — Robert R Raevis
(74) Attorney, Agent, or Firm — Timothy J. Ohara

(57) ABSTRACT

A sample injection method for liquid chromatography is performed with an injection valve having a waste port, two sample loop ports, and two high-pressure ports. One high-pressure port can be connected to a pump and the other high-pressure port can be connected to a chromatography column. A sample loop is connected to one of the sample loop ports on one end and to a pump volume of a sample conveying device on the other end. A section of the sample loop can be separated to facilitate receiving a sample fluid in the sample loop. A control unit controls the injection valve and the sample conveying device. The sample injector allows a sample to be loaded into the sample loop and then pressurized to an operating pressure prior to injecting the sample into the chromatography column. The sample loop
(Continued)

may also be isolated from the operating pressure for facilitating depressurization of the loop.

27 Claims, 9 Drawing Sheets

Related U.S. Application Data

12/863,976, filed as application No. PCT/DE2009/000004 on Jan. 7, 2009, now Pat. No. 8,806,922.

(56) References Cited

U.S. PATENT DOCUMENTS

| | | |
|---|---|---|
| 4,444,066 A | 4/1984 | Ogle et al. |
| 4,939,943 A | 7/1990 | Strohmeier |
| 5,207,109 A | 5/1993 | Olsen |
| 5,637,208 A | 6/1997 | Dourdeville |
| 6,012,487 A | 1/2000 | Hauck |
| 6,155,123 A | 12/2000 | Bakalyar |
| 6,260,407 B1 | 7/2001 | Petro et al. |
| 6,281,019 B1 | 8/2001 | Werringloer |
| 6,382,035 B1 | 5/2002 | Nichols |
| 6,416,663 B1 | 7/2002 | Miroslav et al. |
| 6,475,391 B2 | 11/2002 | Safir et al. |
| 6,874,354 B2 | 4/2005 | Cueni et al. |
| 6,976,383 B2 | 12/2005 | Petro et al. |
| 7,503,203 B2 | 3/2009 | Gamache et al. |
| 9,435,773 B2 * | 9/2016 | Glatz .................. G01N 30/20 |
| 2009/0144520 A1 | 6/2009 | Hochgraeber et al. |
| 2012/0132013 A1 | 5/2012 | Glatz et al. |

* cited by examiner

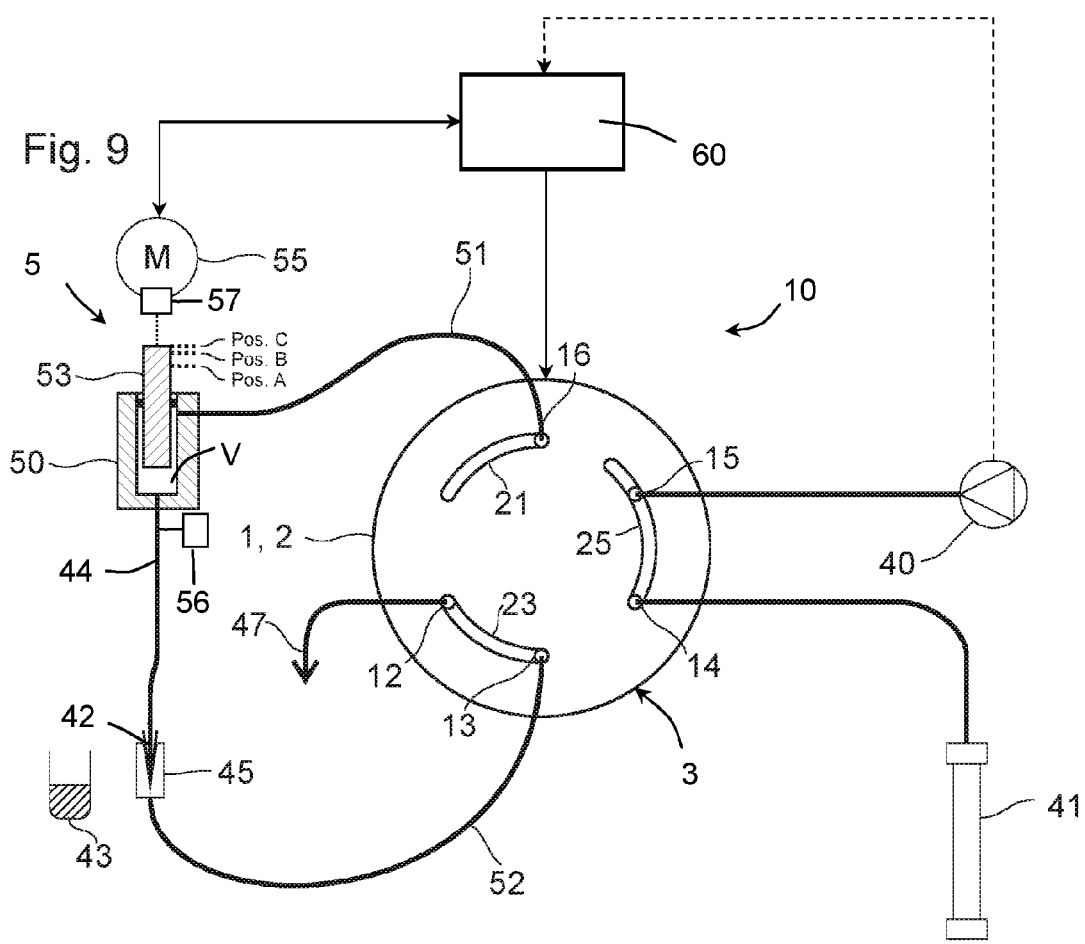

METHODS FOR INJECTING SAMPLES IN LIQUID CHROMATOGRAPHY, PARTICULARLY IN HIGH PERFORMANCE LIQUID CHROMATOGRAPHY

CROSS-REFERENCE TO RELATED APPLICATIONS

This application is a Continuation under 35 U.S.C. § 120 and claims the priority benefit of co-pending U.S. application Ser. No. 14/454,563, filed Aug. 7, 2014, which is a Divisional under 35 U.S.C. § 120 and claims the priority benefit of U.S. application Ser. No. 12/863,976, filed Jul. 21, 2010 now U.S. Pat. No. 8,806,922, which is the United States National Stage Application, under 35 U.S.C. § 371, of International Application PCT/DE2009/000004, filed Jan. 7, 2009, which claims the priority benefit to German Patent Application No. 10 2008 006 266.9, filed Jan. 25, 2008, which applications are hereby incorporated herein by reference in their entireties.

TECHNICAL FIELD OF THE INVENTION

The invention pertains to methods for injecting samples for liquid chromatography, particularly for high performance liquid chromatography (HPLC). The sample injection process provides for pressure compensation during a sample injection sequence, or during a post sample injection sequence, or during both sequences.

BACKGROUND OF THE INVENTION

In HPLC, a sample to be examined needs to be injected into a high-pressure fluid flow, wherein this flow can be interrupted only as briefly as possible. For this purpose, high-pressure injection valves are used that allow a nearly uninterrupted change-over of the fluid flow. Such a design is described, for example, in U.S. Pat. No. 3,530,721. This patent was derived from an original application that was published in 1965.

U.S. Pat. No. 4,939,943 discloses a sample injector with a "high pressure syringe unit." The basic Split Loop Principle of the sample injector disclosed in this application has proven effective in HPLC.

Furthermore, WO 2006/083776 discloses a sample injector for preventing pressure surges that occur during the actuation of the high-pressure valve and could negatively affect the efficiency and the service life of the chromatography column.

During the actuation of the injection valve, compression and decompression volumes flow through the valve with high speeds. According to non-previously-published German Patent Application DE 10 2007 059 651 A1 of the applicant of Dec. 10, 2007, which pertains to a sample injector for high performance liquid chromatography and features a high-pressure change-over valve with optimized service life, these flows cause damage to the high-pressure valve components.

The service life of the high-pressure change-over valve determines the operating costs of an HPLC system. These costs should be maintained as low as possible by minimizing the wear of the high-pressure valve components.

SUMMARY OF THE INVENTION

The invention includes a sample injector for liquid chromatography, particularly for high performance liquid chromatography, in which the injection valve also has an improved service life under extremely high pressures.

Embodiments of the invention apply the Split Loop Principle for a sample injector to facilitate a pressure compensation when the switching positions of the injection valve are changed. The pressure compensation is made possible by an injection valve which features a PRESSURE COMPENSATION position, in which the sample loop ports of the injection valve connected to the ends of the sample loop are not connected to other ports in the injection valve.

In the Split Loop Principle, the sample loop is divided in the connecting piece between the sample conveying device that may be realized, for example, in the form of a syringe and the respective sample loop port of the injection valve. In order to take in the required sample volume or to take in a flushing medium, the end of the intake segment of the separated connecting piece of the sample loop that is connected to the sample conveying device is moved to a sample container or a container for a flushing medium. Subsequently, the divided connecting piece of the sample loop is reconnected such that the sample volume can be injected into the chromatography column by means of the pump in the INJECT position of the injection valve. This basic principle is already described in U.S. Pat. No. 4,939,943. In this case, the special Split Loop Principle provides the advantage that the sample conveying device is flushed with eluent after the injection of the sample such that it is normally not required to flush the sample conveying device, the sample loop and the injection valve after the injection of a sample.

After taking in the sample volume in the LOAD position, the injection valve is, according to one or more embodiments of the invention, changed over into the PRESSURE COMPENSATION position, in which the sample loop ports are shut in a pressure-tight fashion. In this position, the drive of the sample conveying device is controlled in such a way that pressure builds up in the closed sample loop and in the pump volume of the sample conveying device, wherein this pressure essentially corresponds to the pressure, with which the pump feeds the fluid to the chromatography column in the LOAD position or in the INJECT position. Even if the pressure in the sample loop is not identical to the pressure of the pump before the injection valve is changed over from the PRESSURE COMPENSATION position into the INJECT position and a slight differential pressure remains, this slight differential pressure is, according to the invention, maintained so low that it can neither disadvantageously effect the flow through the chromatography column nor cause damage to the injection valve or the chromatography column.

This applies analogously to the change-over from the INJECT position into the LOAD position. In this case, the valve also is initially changed over from the INJECT position into the PRESSURE COMPENSATION position, in which the pressure that essentially corresponds to the pump pressure is reduced until essentially the ambient pressure is reached. If applicable, a slight, harmless differential pressure may also remain in this case when the valve is changed over from the PRESSURE COMPENSATION into the LOAD position.

According to the invention, the pressure compensation (pressure increase or pressure reduction) in the sample loop is achieved by controlling the drive of the sample conveying device accordingly.

In contrast to prior sample injectors, the fluid flows created during the pressure compensation no longer flow through the change-over valve such that damage to valve components due to excessively high flow speeds can no longer occur.

Naturally, this objective also is at least partially attained if the pressure compensation is only carried out in one of the two change-over directions described above.

According to one preferred embodiment of the invention, the two high-pressure ports are connected in the PRESSURE COMPENSATION position of the injection valve. Due to this measure, the flow of the fluid through the chromatography column is maintained and no undesirable peaks can occur in the progression of pressure during the change-over processes.

According to one embodiment of the invention, the injection valve features a rotor and a stator, wherein the rotor features a face that cooperates with the face of the stator and contains at least three grooves that either connect or shut port opening cross sections of the high-pressure ports, the sample loop ports and the waste port arranged in the face of the stator in a pressure-tight fashion as a function of the rotational position of the rotor relative to the stator. The groove that connects the two high-pressure ports in the LOAD position of the injection valve is realized so long that it still connects the high-pressure ports after the stator and the rotor are turned into the PRESSURE COMPENSATION position. This groove therefore is elongated in comparison with the corresponding groove of conventional injection valves.

According to the preferred field of application of the invention, namely in HPLC, the sample conveying device is realized in a high-pressure-resistant fashion and can generate the pressures used in HPLC, preferably pressures greater than 500-600 bar, particularly pressures greater than 1000 bar.

The sample conveying device may feature a movable element that is guided in a pump volume in a sealed fashion and can be moved by means of a drive of the sample conveying device that is controlled by the control unit in order to convey the fluid contained in the pump volume. The sample conveying device may, in particular, be realized in the form of a syringe that is driven by means of a drive, wherein the movable element is formed by the plunger of the syringe.

The control unit can move the plunger or the movable element by a predetermined distance after the PRESSURE COMPENSATION position of the injection valve is reached by controlling the drive accordingly, wherein this predetermined distance suffices for realizing a change of the pump volume of the sample conveying device required due to the elasticities of the devices conveying the fluid and the compressibility of the fluid itself such that a pressure reduction in the sample loop to essentially the ambient pressure can be achieved by increasing the pump volume and a pressure increase in the sample loop to essentially the operating pressure of the pump can be achieved by decreasing the pump volume. The movement of the movable element may take place in a controlled or regulated fashion.

In order to allow a control of the pressure or the ultimate pressure during the pressure compensation in the sample loop, a sensor may be provided that measures the pressure of the fluid in the closed sample loop or in the pump volume of the sample conveying device at least while the injection valve is in the PRESSURE COMPENSATION position.

In this variation, the signal of the pressure sensor is preferably fed to the control unit, wherein the control unit compares the pressure of the fluid with a nominal pressure value and controls the sample conveying device in such a way that the pressure of the fluid reaches a nominal high-pressure value before the injection valve is changed over from the PRESSURE COMPENSATION position into the INJECT position and/or that the pressure of the fluid reaches a nominal low-pressure value before the injection valve is changed over from the PRESSURE COMPENSATION position into the LOAD position.

These and other advantages and features of the invention will be apparent from the following description of the preferred embodiments, considered along with the accompanying drawings.

BRIEF DESCRIPTION OF THE DRAWINGS

The invention is described in greater detail below with reference to the drawings. In these drawings:

FIG. 9 shows the HPLC system of FIG. 8, wherein the injection valve was changed over from the PRESSURE COMPENSATION position into the LOAD position.

DESCRIPTION OF ILLUSTRATIVE EMBODIMENTS

Figure 1:
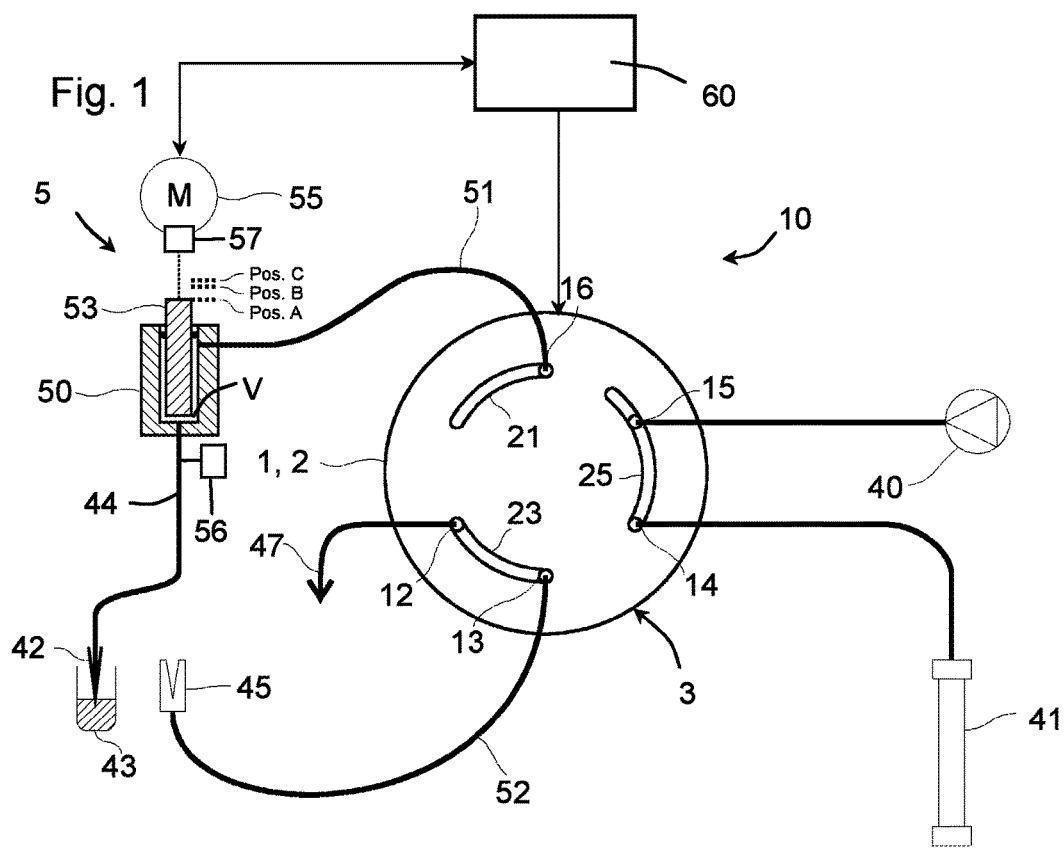
FIG. 1 shows a schematic representation of an HPLC system with a sample injector according to the invention, to which a chromatography column is connected, wherein the injection valve is situated in the LOAD position and the process of taking in a sample volume can begin in the state shown.

FIG. 1 shows a schematic representation of an HPLC system with a sample injector 10 that operates in accordance with the Split Loop Principle and features a sample conveying device 5, an injection valve 3 and a high-pressure pump 40. The sample injector 10 furthermore features a sample loop that includes a first connecting piece 51 and a second connecting piece 52, 44. These may be comprised of a pressure-resistant line with a small diameter, for example in the form of a capillary tube of glass or stainless steel. The connecting piece 51 is connected to a first sample loop port 16 of the injection valve 3 and to the sample conveying device or its pump volume V, respectively. The second connecting piece is comprised of an intake segment 44 and a feed segment 52 and is realized in a separable fashion. For this purpose, the feed segment 52 leads into an injection port 45 that is connected to a second sample loop port 13 of the injection valve 3 via the feed segment 52. The intake segment 44 that is connected to the pump volume V of the sample conveying device 5 with one end features on its other end a sample needle 42, by means of which the intake segment 44 can be connected to the injection port 45.

However, the sample needle 42 can also be moved to a sample container 43 and take in a defined sample volume into the intake segment 44 as described in greater detail below. Furthermore, the sample needle 41 can also be moved to a (not-shown) container for a flushing fluid in order to withdraw flushing fluid for a flushing process and to clean the sample loop 51, 52, 44, the pump volume V and, if applicable, also the ports and the grooves or channels of the injection valve. Due to the special topology of the Split Loop Principle shown, flushing of the sample loop 51, 52, 44 and of the sample conveying device 5 is normally not required because they are flushed during an injection process anyway, namely with eluent supplied by the pump 40. However, the outside of the sample needle 42 can also be cleaned by immersing the needle into a container with cleaning or flushing fluid.

In the embodiment shown, the sample conveying device 5 comprises a syringe 50, in which a plunger 53 is guided in a displaceable and pressure-tight fashion. The plunger 53 is driven by means of a drive 55 that is realized, for example, in the form of a stepping motor. The drive 55 is controlled by a control unit 60. The control unit 60 also controls the change-over processes of the injection valve 3 that features a not-shown controllable drive.

A waste port 12 of the injection valve is connected to a waste line 47, from which fluid can be discharged into a not-shown waste reservoir.

The high-pressure pump 40 is connected to a high-pressure port 15 of the injection valve. A chromatography column 41 is connected to the other high-pressure port 14. The high-pressure pump 40 may be integrated into and form part of the sample injector or be arranged in another unit or a separate pump unit.

The injection valve 3 includes a stator 1 and a rotor 2. The stator 1 features the two high-pressure ports 14, 15, the two sample loop ports 13, 16 and the waste port 12. The injection valve 3 is connected to the other functional elements of the HPLC system via these ports and the above-described connecting lines that may be realized in the form of capillary connections. The high-pressure screw connections required for this purpose are not illustrated in FIG. 1 in order to provide a better overview. For reasons of simplicity, the injection valve is illustrated in the interface between the stator 1 and the rotor 2, wherein the design of the face of the stator 1 and the design of the face of the rotor 2 are shown in order to better comprehend the function of the injection valve. Within the injection valve 3, the ports are realized in the form of bores that lead to the other side of the stator 1. The rotor 2 features a number of arc-shaped grooves 21, 23, 25 that are exactly aligned with the bores of the input and output ports.

The rotor 2 is pressed against the stator with a certain pressing force such that a common interface between the rotor 1 and the stator 2 is formed, at which both components are mutually sealed. In this case, the pressing force is chosen so high that the arrangement also remains sealed at the highest pressures to be expected.

In the first LOAD position of the valve 3 illustrated in FIG. 1, the grooves 21, 23, 25 are aligned relative to the ports 12-16 in such a way that the grooves 23 and 25 respectively connect the two high-pressure ports 14, 15 and the waste port 12 to the sample loop port 13. In this LOAD position, the high-pressure pump 40 therefore conveys fluid in the direction of the chromatography column 41. Furthermore, the sample loop port 16 is closed in a pressure-tight fashion.

Figure 2:
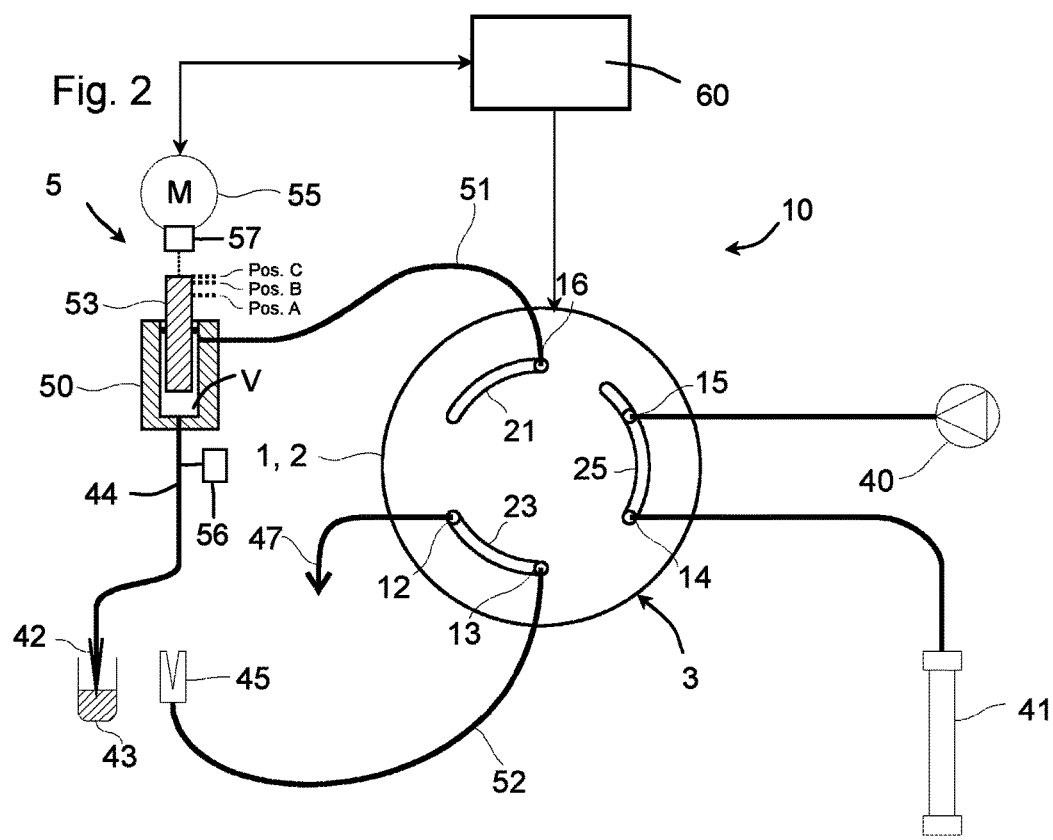
FIG. 2 shows the HPLC system of FIG. 1, wherein the plunger of the syringe was moved into the end position (position C) in order to take in the sample volume.

In the state illustrated in FIG. 1, the sample needle 42 is moved into the sample container 43 such that a sample volume can be taken in. For this purpose, the plunger 53 is situated in the position A and can be moved into the position C by the control unit 60 in order to take in the sample volume. The desired defined sample volume is then withdrawn into the intake segment 44, wherein the volume of the sample is smaller than the volume of the intake segment 44 such that the sample fluid cannot mix with the fluid supplied by the high-pressure pump in the pump volume. FIG. 2 shows the state of the HPLC system after the intake process is completed.

Figure 3:
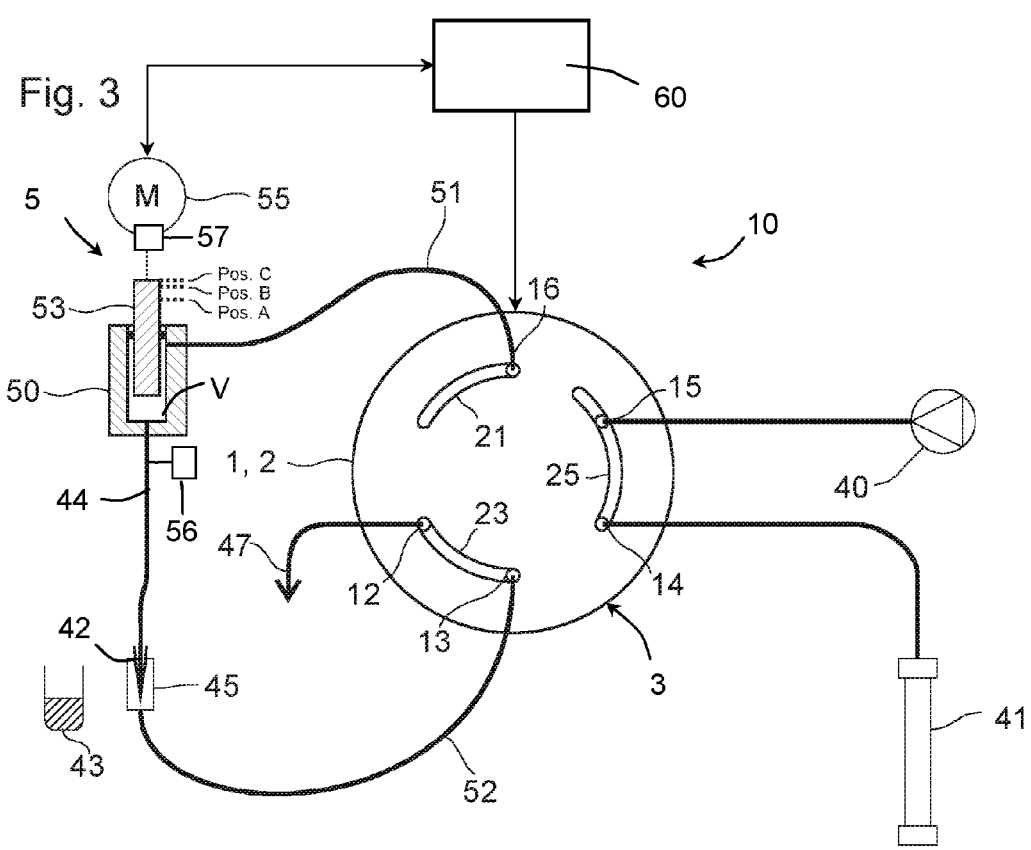
FIG. 3 shows the HPLC system of FIG. 2, wherein the sample needle was moved into the injection port.

In order to inject the sample volume situated in the intake segment 44, the sample needle 42 is moved into the injection port 45. This port seals the needle point in a high-pressure-resistant fashion. This state is illustrated in FIG. 3.

Figure 4:
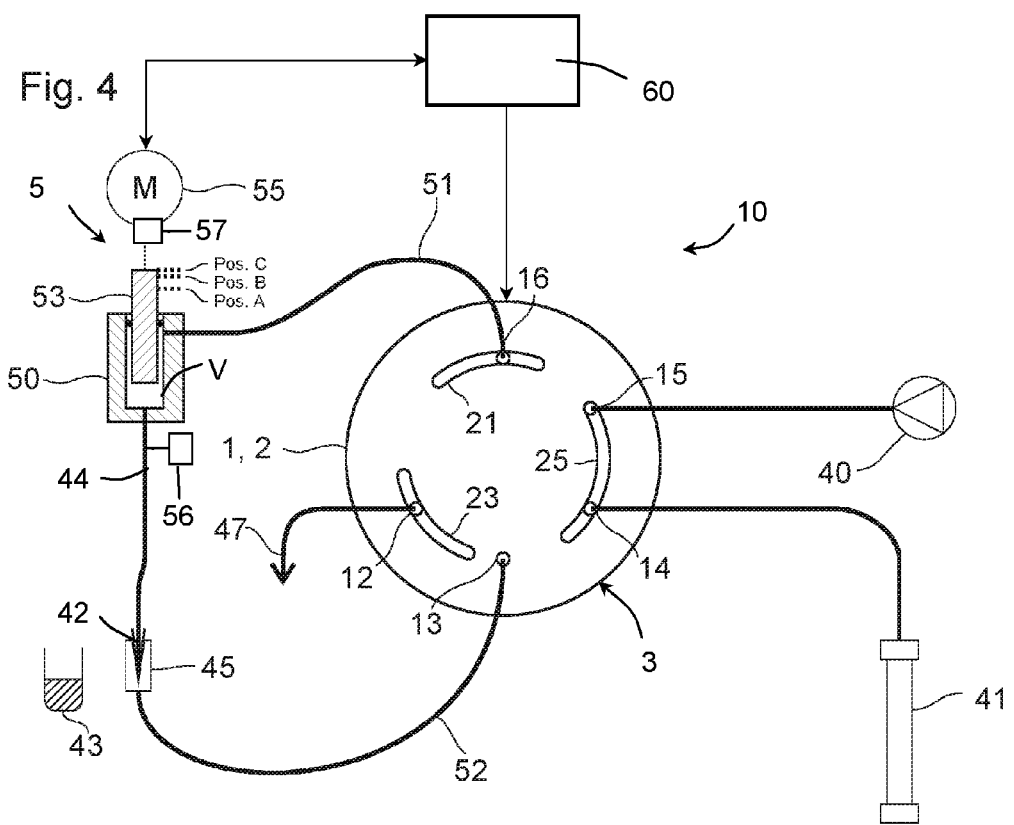
FIG. 4 shows the HPLC system of FIG. 3, wherein the injection valve was changed over from the LOAD position into the PRESSURE COMPENSATION position.

In the next step, the pressure in the sample loop is adjusted to the operating pressure of the chromatography column 41, i.e., to the pressure, with which the high-pressure pump 40 supplies fluid to the inlet of the chromatography column 41. For this purpose, the injection valve is initially changed over into a PRESSURE COMPENSATION position, in which the connecting piece 51 and the second connecting piece or the feed segment 52 of the sample loop are not connected to the other components connected to the injection valve 3 (FIG. 4).

Figure 5:
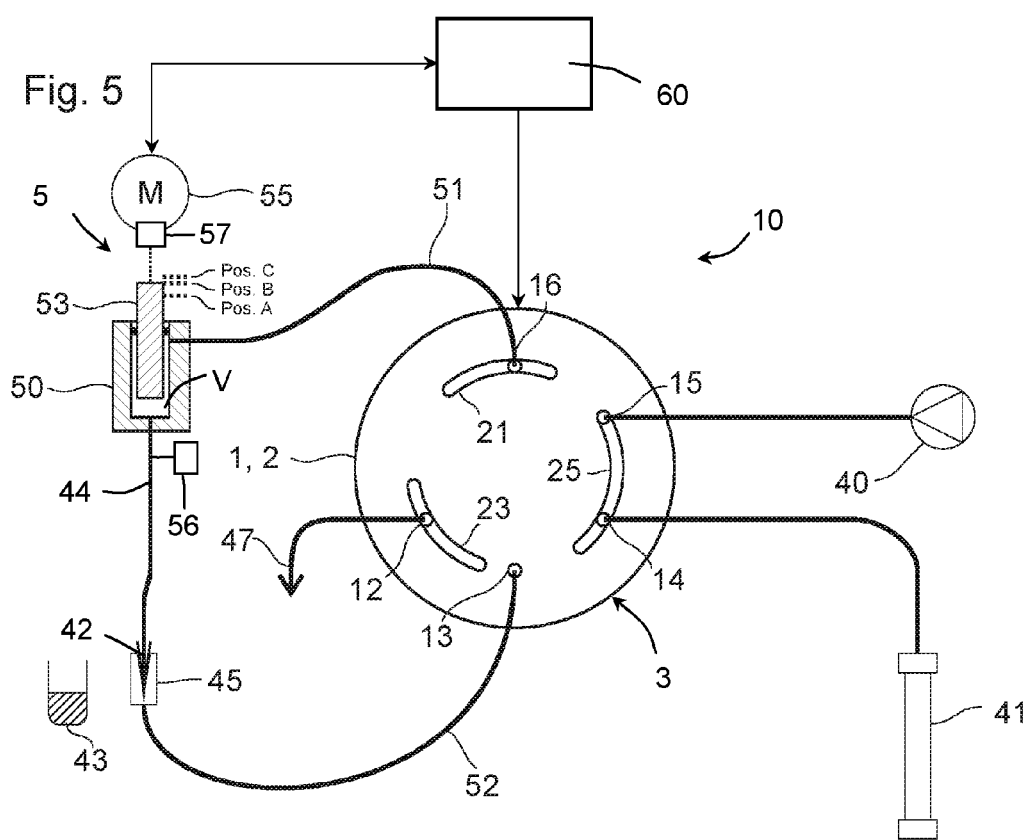
FIG. 5 shows the HPLC system of FIG. 4, wherein the plunger was moved into the position B in order to realize a pressure compensation (pressure increase) in the sample loop.
Figure 6:
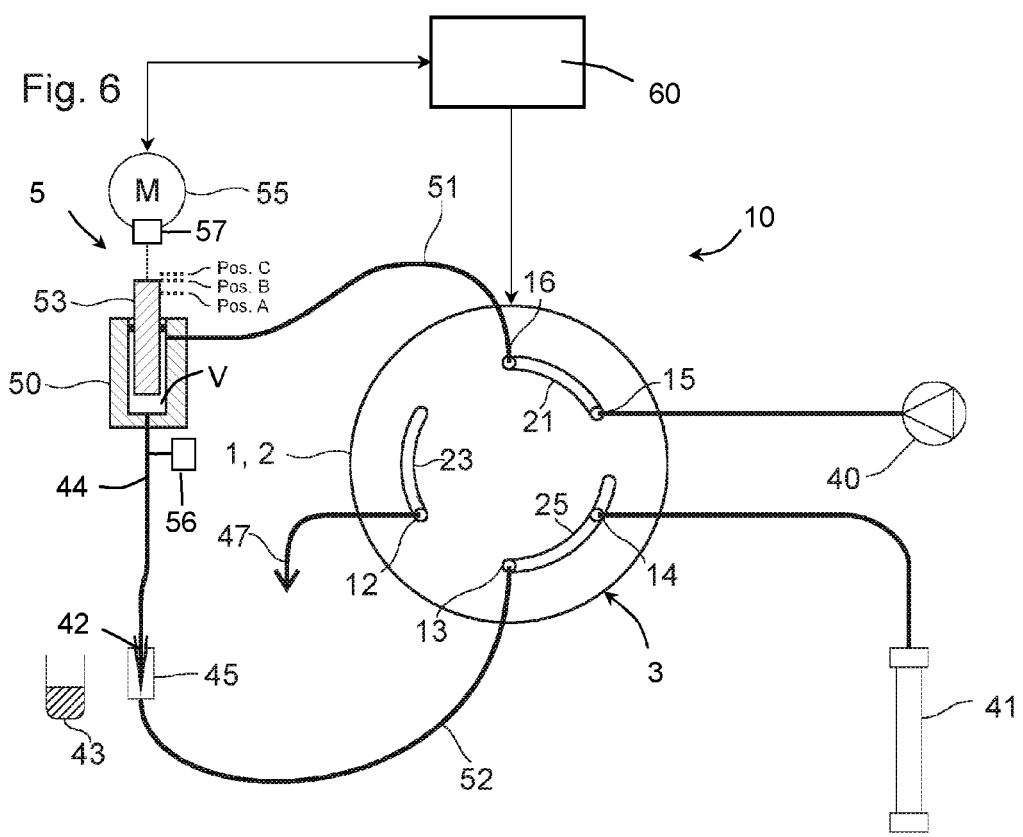
FIG. 6 shows the HPLC system of FIG. 5, wherein the injection valve was changed over from the PRESSURE COMPENSATION position into the INJECT position.

In this PRESSURE COMPENSATION position, the plunger 53 of the high-pressure-resistant sample conveying device is moved into the position B (FIG. 5). In order to prevent an interruption of the flow through the chromatography column 41 while conveying the volume required for the compression of the sample loop content, the groove 25 in the rotor 2 of the valve is realized in a correspondingly elongated fashion such that the two high-pressure ports 14, 15 are still connected in the PRESSURE COMPENSATION position. The travel of the plunger 53 from position C into position B required for building up the pressure can be calculated from the compressibility of the fluid volume enclosed in the sample conveying device 5 and in the sample loop, the elasticity of the arrangement and the current pump pressure. Alternatively, a pressure compensation can be achieved with the aid of a control circuit for the pressure in the high-pressure-resistant sample conveying device. For this purpose, the pressure needs to be measured at a suitable location and the position of the plunger 53 in the sample conveying device 5 needs to be adjusted by the drive 55 in such a way that the pressure corresponds to the required target pressure (=column pressure). Pressure measurement may be realized with a pressure sensor such as sensor 56 or indirectly by means of a force measurement. Conceivable solutions are force measurements on the plunger 53 or in the drive 55. After pressure equality is achieved, the valve is changed over into the INJECT position in order to inject the sample volume into the column 41 (FIG. 6).

In the embodiment shown, the control unit 60 measures the force that the drive 55 needs to exert in order to achieve a corresponding compression in the sample loop. For this purpose, the drive 55 may feature an integrated sensor 57, the signal of which is fed to the control unit 60 (as indicated with a double arrow between the drive 55 and the control unit 60). Due to this measure, the control unit can determine the actual pressure in the pump volume and therefore in the sample loop (the pressure drop in the connecting pieces and in the valve is negligibly small) and adjust this pressure to the desired value.

Figure 7:
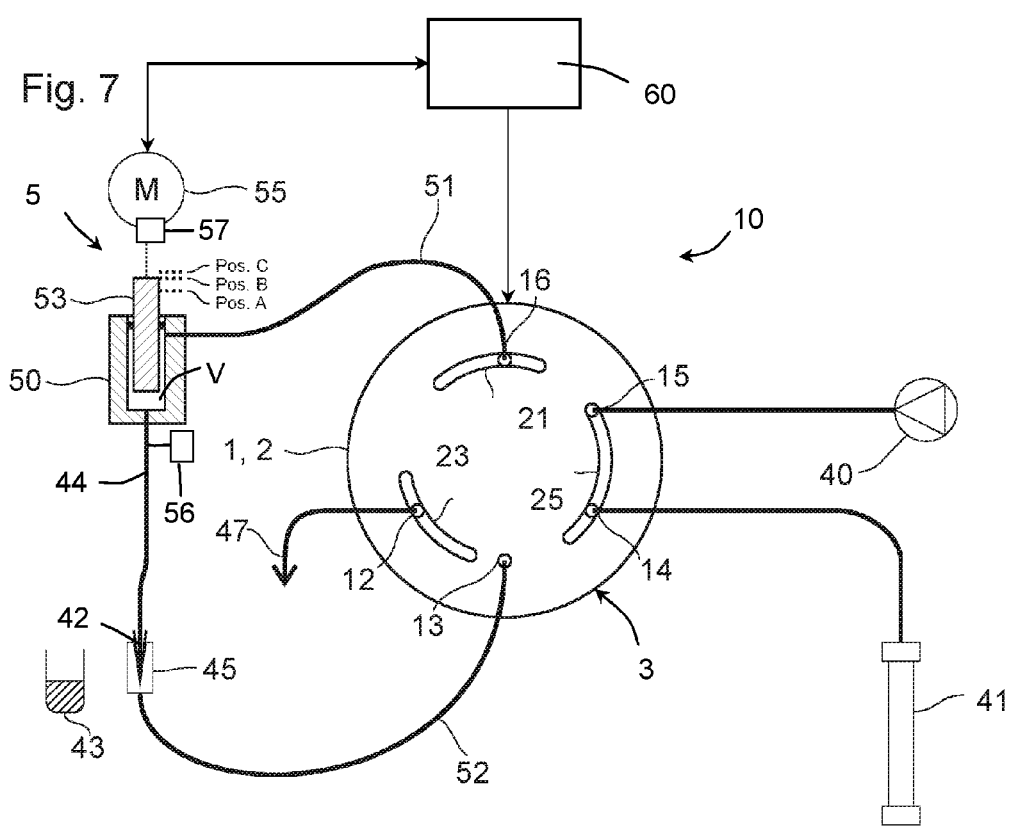
FIG. 7 shows the HPLC system of FIG. 6, wherein the injection valve was changed over from the INJECT position into the PRESSURE COMPENSATION position after the injection of the sample volume.

After the entire sample volume has been conveyed from the intake segment 44 to the column 41 by means of the fluid conveyed by the pump 40, the valve can be once again changed over into the PRESSURE COMPENSATION position in order to decompress the sample loop (FIG. 7).

Figure 8:
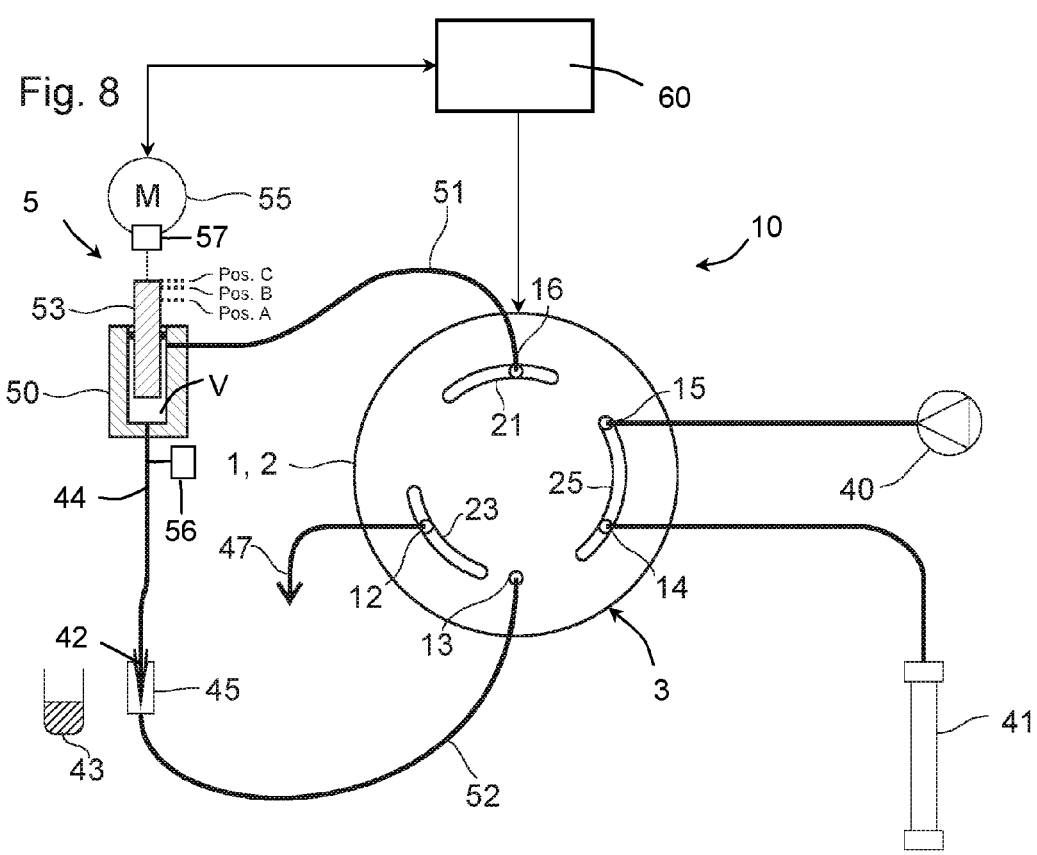
FIG. 8 shows the HPLC system of FIG. 7, wherein the plunger was moved into the end position (position C) in order to realize a pressure compensation (pressure reduction)

The plunger 53 is moved from the position illustrated in FIG. 7 into position C. This causes the pressure in the sample loop to be adjusted to the atmospheric pressure. This state of the HPLC system is illustrated in FIG. 8. During this decompression time in the PRESSURE COMPENSATION position of the injection valve 3, the column 41 is already connected to the pump 40 via the elongated groove 25 in order to prevent pressure drops. The travel of the plunger 53 from position B to position C can either be calculated analogous to the compression in FIG. 5 or determined by measuring and controlling the pressure. Alternatively, the pressure can also be determined indirectly by means of a force measurement on the plunger 53 or on the drive 55 of the plunger.

After the sample loop has been decompressed, the valve 3 is changed over into the LOAD position (FIG. 9). No damaging flows in the injection valve occur during this process.

The plunger 53 of the high-pressure-resistant sample conveying device 5 can now be moved back into the starting position A. The excess quantity of fluid is discharged via the waste connection 47. The unpressurized needle 42 can subsequently be moved from the needle seat of the injection port 45 to the corresponding sample bottle in order to take in the next sample.

The position C during the decompression may also differ from the starting position A prior to the compression. For example, if gradients (time-controlled mixing ratio of the eluent) are pumped through the column, the position C at the end of the decompression may differ because the compressibility of the loop content may have changed.

The control unit 60 can store predetermined positions A, B, C and/or differences in the distance between these positions as a function of parameters of the entire sample injector, particularly the compressibility of the eluent, elasticity properties of the sample loop and the sample conveying device, etc. The plunger can then be automatically moved into these positions (i.e., without a control) or these positions may serve as approximate values or initial values for a controlled movement.

In order to determine the positions A, B, C and the respective travel of the plunger, a change-over of the injection valve 3 may be carried out without compression or decompression, respectively. The pressure drop can then be determined by means of a pressure sensor and the required travel as well as the respective positions B or C can be determined based on this pressure drop. The thusly determined values can then be stored and used for other change-over processes, in which a compression or decompression takes place. A corresponding sensor may also be provided in the pump 40. Pumps of this type for HPLC always feature a pressure sensor for controlling the conveyed eluent anyway. The compressibility of the medium, particularly of the eluent, can also be determined by means of the pump 40. Such pumps are realized, for example, in the form of dual-plunger pumps, in which the change-over from one plunger to the other plunger is suitably controlled or regulated by means of a pressure sensor and a control unit in such a way that a highly constant flow rate is achieved. Since the compressibility of the medium also needs to be taken into account during this change-over process, the compressibility can be determined by suitably controlling the dual-plunger pump during the change-over from one plunger to the other plunger and fed to the control unit 60 as information. This connection between the pump 40 and the control unit 60 is merely illustrated with broken lines in FIG. 9.

In the automatic sample injector shown, it is therefore ensured that the pressure in the sample loop is adjusted to the current operating pressure of the chromatography column by means of decompression in the sufficiently (high) pressure-resistant sample conveying device when the injection valve is in a special intermediate position, namely the PRESSURE COMPENSATION position, before the intake segment is moved into the flow path toward the chromatography column, i.e., before the injection valve is changed over into the INJECT position.

In addition, the pressure in the sample loop is adjusted to the atmospheric pressure (decompression) in the same intermediate position of the injection valve, namely the PRESSURE COMPENSATION position, by taking in an exactly defined additional fluid quantity into the sample conveying device before the sample loop is separated in order to take in a sample volume from a sample container, i.e., before the injection valve is changed over into the LOAD position.

The compression and decompression volumes do not flow through the injection valve. Consequently, the service life of the (high-pressure) injection valve of the sample injector is only limited by the unavoidable abrasion between the rotor and the stator and, if applicable, the abrasive effect, for example, of dirt particles or sample material.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A method of operating a liquid chromatography system, the liquid chromatography system comprising a liquid chromatography column and an injection valve, the method comprising:

isolating a sample loop of the liquid chromatography system from a high-pressure fluidic path in fluid communication with the liquid chromatography column, wherein the high-pressure fluidic path is at a pump pressure, wherein the sample loop is in fluid communication with the injection valve and the sample loop comprises a sample conveying device, and isolating the sample loop comprises placing the injection valve in a PRESSURE COMPENSATION position, wherein a volume of the sample conveying device is defined by a cavity in which a movable element is slidably mounted;

calculating a distance for a movement of the movable element within the cavity from a first position to a second position to increase a pressure in the sample loop from an essentially ambient pressure to the pump pressure based on one or more of a compressibility of a fluid in the sample loop, an elasticity of the sample loop, and the pump pressure; and while the sample loop is isolated from the high-pressure fluidic path, decreasing the volume of the sample conveying device to increase the pressure in the sample loop from the essentially ambient pressure to essentially correspond to the pump pressure of the high-pressure fluidic path, wherein decreasing the volume includes sliding the movable element within the cavity by the calculated distance from the first position to the second position.

2. The method of claim 1, wherein at the PRESSURE COMPENSATION position,
(i) first and second sample loop ports of the injection valve are closed so as to facilitate a pressurization of the sample loop, and
(ii) first and second high-pressure ports of the injection valve are connected so as to operatively connect a high-pressure pump in fluid communication with the high-pressure fluidic path to the liquid chromatography column.

3. The method of claim 2 further comprising:
determining the compressibility of the fluid with the high-pressure pump.

4. The method of claim 1, wherein placing the injection valve in the PRESSURE COMPENSATION position includes rotating a rotor of the injection valve with respect to a stator of the injection valve.

5. The method of claim 1 further comprising:
operating the injection valve to connect the sample loop to the high-pressure fluidic path such that the pump pressure from a high-pressure pump of the liquid chromatography system is applied to the sample loop, and a sample in the sample loop flows from the sample loop into the high-pressure fluidic path and to the chromatography column.

6. The method of claim 5 further comprising:
after operating the injection valve to connect the sample loop, introducing the sample into the chromatography column;
isolating the sample loop from the high-pressure fluidic path by placing the injection valve back in the pressure compensation position; and
increasing the volume of the sample conveying device to reduce the pressure in the sample loop from the pump pressure of the liquid chromatography column to the essentially ambient pressure.

7. The method of claim 1, in which the compressibility of the fluid and the elasticity of the sample loop are stored in a control unit of the liquid chromatography system.

8. The method of claim 1, in which the moveable element includes a plunger.

9. The method of claim 2, in which the sample loop includes a first connecting piece and a second connecting piece, in which the first connecting piece is connected to the first sample loop port of the injection valve and to the sample conveying device, in which the second connecting piece is connected to the second sample loop port of the injection valve and to the sample conveying device, in which the second connecting piece includes an intake segment and a feed segment, in which the intake segment and the feed segment are configured to be separated.

10. A method of injecting a sample in a liquid chromatography system, the method comprising:
isolating a sample loop of the liquid chromatography system from a high-pressure fluidic path of the liquid chromatography system, the high-pressure fluidic path at a pump pressure in fluid communication with a liquid chromatography column of the liquid chromatography system, wherein the high-pressure fluidic path is at a pump pressure, wherein the sample loop comprises a sample conveying device, wherein a volume of the sample conveying device is defined by a cavity in which a movable element is slidably mounted;
calculating a distance for a movement of the movable element within the cavity from a first position to a second position to increase a pressure in the sample loop from an essentially ambient pressure to the pump pressure based on one or more of a compressibility of a fluid in the sample loop, an elasticity of the sample loop, and the pump pressure;
placing the sample in the sample loop;
with the sample placed in the sample loop and with the sample loop remaining isolated from the high-pressure fluidic path, decreasing the volume of the sample conveying device to increase the pressure in the sample loop from the essentially ambient pressure to essentially correspond to the pump pressure of the high-pressure fluidic path, wherein the movable element within the cavity is moved by the calculated distance from the first position to the second position; and
connecting the sample loop to the high-pressure fluidic path so that the pump pressure from a high-pressure pump is applied to the sample loop to cause the sample in the sample loop to flow from the sample loop through a portion of the high-pressure fluidic path to the chromatography column.

11. The method of claim 10 further including:
isolating the sample loop from the high-pressure fluidic path of the liquid chromatography system after the sample has flowed into the high-pressure fluidic path; and
(b) increasing the volume of the sample conveying device to reduce the pressure in the sample loop to the essentially ambient pressure.

12. The method of claim 10 wherein isolating the sample loop from the high-pressure loop includes placing an injection valve in a PRESSURE COMPENSATION position in which
first and second sample loop ports of the injection valve are closed so as to facilitate pressurization of the sample loop, and
first and second high-pressure ports of the injection valve are connected so as to operatively connect the high-pressure pump to the liquid chromatography column.

13. The method of claim 12 wherein placing the injection valve in the PRESSURE COMPENSATION position includes rotating a rotor of the injection valve with respect to a stator of the injection valve.

14. The method of claim 12 further comprising:
determining the compressibility of the fluid with the high-pressure pump.

15. The method of claim 12, in which the sample loop includes a first connecting piece and a second connecting piece, in which the first connecting piece is connected to the first sample loop port of the injection valve and to the sample conveying device, in which the second connecting piece is connected to the second sample loop port of the injection valve and to the sample conveying device, in which the second connecting piece includes an intake segment and a feed segment, in which the intake segment and the feed segment are configured to be separated.

16. The method of claim 10 wherein the movable element is connected to a drive device which is operable to move the movable element within the cavity, and the method further comprises: measuring a force exerted upon the movable element by the drive device.

17. The method of claim 10, in which the compressibility of the fluid and the elasticity of the sample loop are stored in a control unit of the liquid chromatography system.

18. The method of claim 10, in which the moveable element includes a plunger.

19. A method of operating a liquid chromatography system, the liquid chromatography system comprising a liquid chromatography column and an injection valve, the method comprising:
  isolating a sample loop of the liquid chromatography system from a high-pressure fluidic path in fluid communication with the liquid chromatography column, wherein the high-pressure fluidic path is at a pump pressure, wherein the sample loop is in fluid communication with the injection valve and the sample loop comprises a sample conveying device, and isolating the sample loop comprises placing the injection valve in a PRESSURE COMPENSATION position, wherein the sample conveying device comprises a syringe and a movable element in the syringe;
  calculating a distance for a movement of the movable element within the syringe from a first position to a second position to increase a pressure in the sample loop from an essentially ambient pressure to the pump pressure based on one or more of a compressibility of a fluid in the sample loop, an elasticity of the sample loop, and the pump pressure; and
  while the sample loop is isolated from the high-pressure fluidic path, sliding the movable element within the syringe by the calculated distance from the first position to the second position to increase the pressure in the sample loop from the essentially ambient pressure to essentially correspond to the pump pressure of the high-pressure fluidic path.

20. The method of claim 19, wherein at the PRESSURE COMPENSATION position,
  (i) first and second sample loop ports of the injection valve are closed so as to facilitate a pressurization of the sample loop, and
  (ii) first and second high-pressure ports of the injection valve are connected so as to operatively connect a high-pressure pump in fluid communication with the high-pressure fluidic path to the liquid chromatography column.

21. The method of claim 20 further comprising:
  determining the compressibility of the fluid with the high-pressure pump.

22. The method of claim 20, in which the sample loop includes a first connecting piece and a second connecting piece, in which the first connecting piece is connected to the first sample loop port of the injection valve and to the sample conveying device, in which the second connecting piece is connected to the second sample loop port of the injection valve and to the sample conveying device, in which the second connecting piece includes an intake segment and a feed segment, in which the intake segment and the feed segment are configured to be separated.

23. The method of claim 19, wherein placing the injection valve in the PRESSURE COMPENSATION position includes rotating a rotor of the injection valve with respect to a stator of the injection valve.

24. The method of claim 19 further comprising:
  operating the injection valve to connect the sample loop to the high-pressure fluidic path such that the pump pressure from a high-pressure pump of the liquid chromatography system is applied to the sample loop, and a sample in the sample loop flows from the sample loop into the high-pressure fluidic path and to the chromatography column.

25. The method of claim 24 further comprising:
  after operating the injection valve to connect the sample loop, introducing the sample into the chromatography column;
  isolating the sample loop from the high-pressure fluidic path by placing the injection valve back in the pressure compensation position; and
  sliding the movable element within the syringe from the second position to the first position to decrease the pressure in the sample loop to the essentially ambient pressure.

26. The method of claim 19, in which the compressibility of the fluid and the elasticity of the sample loop are stored in a control unit of the liquid chromatography system.

27. The method of claim 19, in which the moveable element includes a plunger.

* * * * *

(12) SUPPLEMENTAL EXAMINATION CERTIFICATE

United States Patent  
Hochgraeber

(10) Number: US 10,031,112 F1  
(45) Certificate Issued: Feb. 13, 2020

Control No.: 96/000,304  
Primary Examiner: Ling Xu

Filing Date: Jan. 27, 2020

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 9,435,773 B2 | 9/2016 | Glatz et al. |